United States Patent [19]
Tiedemann et al.

[11] 3,964,870
[45] June 22, 1976

[54] DIAGNOSTIC COMPOSITION FOR THE DETERMINATION OF GLUCOSE

[75] Inventors: Hugo Tiedemann, Mannheim-Wallstadt; Bernward Sojka, Viernheim; Hans Lange, Lampertheim; Hans-Georg Rey; Peter Rieckmann, both of Mannheim-Waldhof, all of Germany

[73] Assignee: Boehringer Mannheim G.m.b.H., Mannheim-Waldhof, Germany

[22] Filed: Mar. 4, 1975

[21] Appl. No.: 555,327

[30] Foreign Application Priority Data
Mar. 29, 1974   Germany............................ 2415257

[52] U.S. Cl............................ 23/253 TP; 23/DIG. 2; 195/103.5 C
[51] Int. Cl.² ................. G01N 31/14; G01N 31/22; G01N 33/16
[58] Field of Search ........... 23/253 TP, 230, DIG. 2; 195/103.5 C

[56]        References Cited
         UNITED STATES PATENTS
2,848,308   8/1958   Free ............................... 23/253 TP
3,050,373   8/1962   Collins ........................... 23/253 TP
3,072,539   1/1963   Fancher et al. .............. 195/103.5 C
3,104,209   9/1963   Scott............................. 195/103.5 C
3,232,710   2/1966   Rieckmann et al. ............ 23/253 TP
3,802,842   4/1974   Lange et al. .................... 23/253 TP

OTHER PUBLICATIONS

Yamazaki, et al., Chem. Abstr. 72, 96630r (1970).

Podsiadly et al., Chem. Abstr. 72, 11138p (1970).

Morris J. E., Chem. Abstr. 75, 60941r (1971).

Jones et al., Chem. Abstr. 78, 12201q (1973).

Child et al., Chem. Abstr. 80, 130397x (1974).

*Primary Examiner*—Robert M. Reese
*Attorney, Agent, or Firm*—Burgess, Dinklage & Sprung

[57]        ABSTRACT

Glucose contained in urine is determined by contacting a sample with a diagnostic composition comprising an absorbent carrier impregnated with glucose oxidase, peroxidase, an indicator compound such as o-tolidine, and as a buffer, 2-(N-morpholino)-ethanesulfonic acid.

10 Claims, No Drawings

DIAGNOSTIC COMPOSITION FOR THE DETERMINATION OF GLUCOSE

The present invention is concerned with a diagnostic agent for the detection of glucose in urine.

The detection of glucose in urine is of great importance for the diagnosis of diabetes and for the continuous control thereof. In view of this fact, a large number of so-called rapid tests for glucose in urine have been described in the patent literature and some of these tests are commercially available. They are based almost exclusively on the following principle: glucose is oxidized by means of glucose oxidase and oxygen to give gluconic acid and hydrogen peroxide and this latter oxidizes an indicator, by means of peroxidase, to give a colored compound. Although a number of such indicators have previously been described, hitherto o-tolidine has been preponderantly used.

In general, such a glucose test is carried out at a pH of 4 to 7, which is adjusted with the conventional buffers, such as phosphate, citrate and similar buffers. However, a pH of 5 is almost exclusively preferred since, at this pH, the sensitivity and the color graduation is apparently optimum (see, for example, U.S. Pat. Nos. 3,050,373 and 2,848,308, as well as German patent specification No. 1,598,809). However, test papers with this pH value suffer from the serious disadvantage that the reaction colors are, in the case of the so-called "diabetic ketoacidosis," weakened and can even be completely suppressed. In the case of ketoacidosis, comparatively large amounts of acetoacetic acid and of hydroxybutyric acid occur in the urine, which disturbs the reaction of test papers with a buffer of pH 5. Ketoacidosis mainly occurs in the case of diabetes but can also occur in other diseases and in hunger states. "Diabetic Ketoacidosis" is distinguished from other forms of ketoacidosis by the simultaneous appearance of glucose in the urine. A rapid test for glucose which is disturbed by the ketoacidosis is, therefore, not suitable either for the differential diagnosis of ketoacidosis or for the diagnosis and continuous control of diabetes.

Our investigations have shown that by reduction of the pH value of the glucose test paper to 5.8 to 6.2 and preferably to about 6.0, disturbances in the case of ketoacidosis can be reduced. However, when using conventional buffers, it has been shown that the graduation of the color reaction is very considerably impaired, without the disturbance being avoided in all cases. Furthermore, the storage stability of the test papers leaves much to be desired in many cases.

Surprisingly, we have now found that glucose test papers can be obtained which are sensitive and react quickly and with good color graduation and are also not disturbed in the case of ketoacidosis.

Essentially, the invention comprises diagnostic agents containing an absorbent carrier impregnated with glucose oxidase, peroxidase, an indicator and, as a buffer, 2-(N-morpholino)-ethane-sulfonic acid (MES). These glucose test papers containing MES are completely stable even when subjected to the action of elevated temperatures for comparatively long periods of time, which is of considerable importance in the case of use in the tropics.

2-(N-morpholino)-ethane-sulfonic acid is a known buffer; it was introduced by Good (Biochemistry, 5, 467/1966) for work with biological systems but was used exclusively in the liquid phase and not for solid reagent preparations, such as test papers. The surprising effects of this special buffer when used for test papers certainly was not to have been foreseen since other buffers employed in biological systems, such as the so-called tris buffer, do not show actions comparable to those of MES, as can be seen from the results given in the following Table 1:

TABLE 1

| buffer (pH 6.0) | reaction color with 100–1000 mg.% glucose in urine | disturbance by 250 mg.% acetoacetic acid and 2000 mg.% β-hydroxybutyric acid in urine | decrease of reaction after 30 days at 60°C. |
|---|---|---|---|
| MES, 0.5M (cf.Example 1) | bright green to blue-black | no disturbance | practically no decrease |
| phosphate, 0.25M | bright green to grey-green | moderate disturbance | very strong decrease |
| citrate, 0.25M | bright green to grey-green | moderate disturbance | strong decrease |
| citrate, 0.5M | bright green to dark green | moderate disturbance | strong decrease |
| tris-citrate, 0.5M | bright green to green | slight disturbance | strong decrease |
| imidazole, 0.25M | bright green to grey-green | strong disturbance | very strong decrease |
| 3-aminopyridine, 0.5M | green-yellow to bright green | slight disturbance | no more reaction |
| malonate, 0.5M | grey-green to dark green | slight disturbance | strong decrease |
| maleate, 0.125M | bright green to grey-green | slight disturbance | moderate decrease |
| pyrophosphate, 0.25M | bright green to dark green | slight disturbance | very strong decrease |
| comparison with pH 5: citrate, 0.25M | dark green to blue-black | strong disturbance | slight decrease |

As can be seen from the above Table, only MES provides, as buffer substance, optimum test papers in every regard. With conventional and even with unusual buffer substances, test papers are obtained which, in some cases, display considerable disturbances due to the presence of acetoacetic acid and hydroxybutyric acid (i.e. in the case of ketoacidosis) and, furthermore are less sensitive and/or less storage stable.

Thus, the present invention provides a diagnostic agent for the detection of glucose in urine, comprising an absorbent carrier which is impregnated with glucose oxidase, peroxidase, an indicator and a buffer, the buffer being 2-(N-morpholino)-ethane-sulfonic acid.

The MES buffer used according to the present invention can be used in concentrations of 25 to 75 mMol, preferably of about 50 mMol, per 100 ml. impregnation solution. The desired pH range of 5.8 to 6.2 and preferably of about 6.0, is obtained when an aqueous slurry of 2-(N-morpholino)-ethane-sulfonic acid is mixed with the necessary amount of concentrated aqueous sodium hydroxide solution. In the desired pH range, a homogeneous solution is thereby obtained. Besides glucose oxidase, peroxidase and an indicator (preferably o-tolidine), which are employed in the conventional concentrations, there can also be used adjuvants, such as solubilizing agents (e.g. polyvinyl-pyrrolidone or polyethylene glycol) and wetting agents (e.g. sodium lauroyl sarcosinate or sodium lauryl sulfate), in the production of the test papers. Similarly, an addition of yellow colored materials (e.g. tartrazine or naphthol yellow S) can be advantageous since they make the color change more clearly visible.

As absorbent carriers for the test papers, it is preferred to use filter papers but fleece and felts of cellulose or of synthetic resins can also be employed.

For the production of a preferred embodiment of the new diagnostic agent according to the present invention, an absorbent carrier, preferably filter paper, is impregnated with a solution which contains the above-given components and subsequently dried.

As solvents for the impregnation solution, it is especially preferred to use mixtures of water and readily volatile organic solvents, for example lower alcohols.

Test papers obtained in this manner can be used as such, after having been cut up into strips. If desired, the paper strips can also be sealed between synthetic resin films (see German patent specification No. 1,546,307) or sealed or stuck on to such films. However, they are preferably sealed between a synthetic resin film and a fine-mesh material in the manner described in German patent specification No. 2,118,455.

The following Examples are given for the purpose of illustrating without limiting, the present invention:

EXAMPLE 1

Filter paper (Schleicher & Schüll 597 NF) was impregnated with a solution of the following composition and then dried at 50°C.:

| | |
|---|---|
| glucose oxidase | 222 mg. |
| peroxidase | 28 mg. |
| MES buffer (pH 6.0; 1.0M aq. solution) | 50 ml. |
| tartrazine | 80 mg. |
| o-tolidine | 420 mg. |
| ethanol | 33 ml. |
| distilled water | ad 100 ml. |

The test papers thus obtained reacted with urines which contained from 50 to 1000 mg.% glucose with bright green to blue-black color shades, with good color graduations. Urines which additionally contained 250 mg.% acetoacetic acid and about 2000 mg.% β-hydroxybutyric acid showed practically the same color reactions. Furthermore, no change was observed after the test papers had been stored for 15 days at 60°C. or for 4 months at 40°C.

EXAMPLE 2

Filter paper (Whatman No. 6) was impregnated with a solution of the following composition and then dried at 50°C.:

| | |
|---|---|
| glucose oxidase | 222 mg. |
| peroxidase | 28 mg. |
| MES buffer (pH 5.8; 1.0M aq. solution) | 65 ml. |
| tartrazine | 80 mg. |
| polyvinyl-pyrrolidone | 300 mg. |
| o-tolidine | 420 mg. |
| ethanol | 30 ml. |
| distilled water | ad 100 ml. |

The test paper thus obtained had practically the same properties as the test paper according to Example 1.

EXAMPLE 3

Filter paper (Schleicher & Schüll 595) was impregnated with a solution of the following composition and then dried at 50°C.:

| | |
|---|---|
| glucose oxidase | 222 mg. |
| peroxidase | 28 mg. |
| MES buffer (pH 6.2; 1.0M aq. solution) | 25 ml. |
| sodium lauroyl sarcosinate | 100 mg. |
| naphthol yellow S | 100 mg. |
| o-tolidine | 420 mg. |
| ethanol | 33 ml. |
| distilled water | ad 100 ml. |

The test paper thus obtained also had practically the same properties as the test paper according to Example 1.

It will be appreciated that the instant specification and examples are set forth by way of illustration and not limitation, and that various modifications and changes may be made without departing from the spirit and scope of the present invention.

In the above examples, the indicator compound is o-tolidine. However, many other compounds may also be used which are oxidised to dyestuffs with hydrogen peroxide and peroxidase as catalyst. Preferred compounds of this type include, for example, the Nadi reagents, p-phenylene-diamine derivatives, guaiac resin, azines and the like. Most preferred is the use of benzidine, o-dianisidine and o-tolidine.

What is claimed is:

1. Diagnostic agent for the detection of glucose in urine, comprising an absorbent carrier impregnated with glucose oxidase, peroxidase, an indicator compound and, as a buffer, 2-(N-morpholino)-ethane-sulfonic acid.

2. Diagnostic agent as claimed in claim 1, wherein the absorbent carrier is filter paper.

3. Diagnostic agent as claimed in claim 1, wherein said indicator compound is o-tolidine.

4. Diagnostic agent as claimed in claim 1 also containing a solubilizing agent or a wetting agent.

5. Diagnostic agent as claimed in claim 1, wherein a yellow colored material is additionally present.

6. Diagnostic agent as claimed in claim 1, wherein the impregnated absorbent carrier is sealed between two synthetic resin films.

7. Diagnostic agent as claimed in claim 1, wherein the impregnated absorbent carrier is sealed or adhered to a synthetic resin film.

8. Diagnostic agent as claimed in claim 1, wherein the impregnated absorbent carrier is sealed between a synthetic resin film and a fine-mesh material.

9. Diagnostic agent as claimed in claim 1, wherein the pH value of the buffer is between 5.8 and 6.2.

10. Diagnostic agent as claimed in claim 9, wherein the pH value of the buffer is about 6.0.

* * * * *